United States Patent [19]

Moellering et al.

[11] Patent Number: 5,426,034
[45] Date of Patent: Jun. 20, 1995

[54] PROCESS FOR THE PRODUCTION AND USE OF A STABLE 6-PHOSPHOGLUCONOLACTONASE

[75] Inventors: Hans Moellering, Tutzing; Georg-Burkhard Kresse, Penzberg, both of Germany

[73] Assignee: Boehringer Mannheim GmbH, Mannheim, Germany

[21] Appl. No.: 22,873

[22] Filed: Feb. 25, 1993

Related U.S. Application Data

[63] Continuation of Ser. No. 756,218, Sep. 4, 1991, abandoned.

[30] Foreign Application Priority Data

Sep. 5, 1990 [DE] Germany ............... 40 28 086.1

[51] Int. Cl.$^6$ ............... C12Q 1/34; C12Q 1/48; C12Q 1/50
[52] U.S. Cl. ............... 435/18; 435/15; 435/17; 435/814
[58] Field of Search ............... 435/15, 17, 18, 814, 435/822

[56] References Cited

U.S. PATENT DOCUMENTS 3,907,644  9/1975  Mollering et al. ............ 195/99
4,740,488  4/1988  Rondo ............ 435/15

FOREIGN PATENT DOCUMENTS 0043181  1/1982  European Pat. Off. .
0328380  8/1989  European Pat. Off. .

OTHER PUBLICATIONS

Bauer, H. P. 6-phosphogluconolactonase Eur J Biochem 133, 163–168 (1983).
Medina-Puerta M. M. Purification of 6-PGL Biochem Int 1988 17(6) 1011–1019.
Beutler E. et al., Brit. Journal of Haemat., vol. 62/No. 3 (1986), 557–586.
Beutler, E. and Kuhl W., J. Lab. Clin. Med., vol 107/6 (1986), 502–507.
Gerhardt, Methods of Enzymatic Analysis, Third Edition, vol. III, "Enzymes 1: Oxidoreducases, Transferases", pp. 510–539, 1983.

*Primary Examiner*—Michael G. Wityshyn
*Assistant Examiner*—Ralph Gitomer
*Attorney, Agent, or Firm*—Nikaido Marmelstein, Murray & Oram

[57] ABSTRACT

The invention concerns a new 6-phosphogluconolactonase which has an enzyme activity of at least 90% with respect to the initial activity after about 20 hours at pH 7.0 and 20° C. In addition a process is described for the production of the enzyme from Leuconostoc. The enzyme is preferably suitable for the determination of ATP or reaction partners which can be converted into 6-phosphogluconolactone.

16 Claims, 3 Drawing Sheets

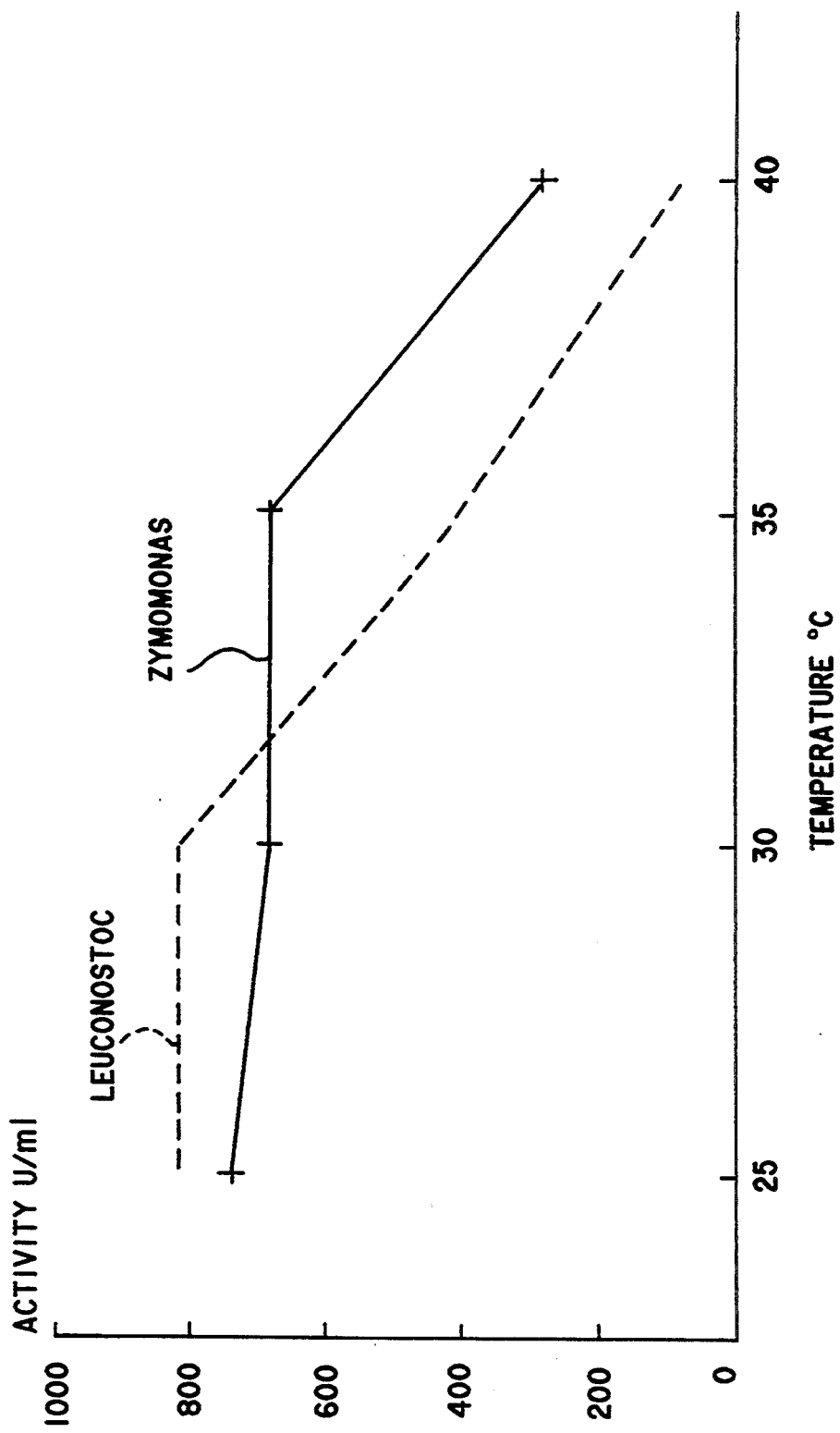

PROCESS FOR THE PRODUCTION AND USE OF A STABLE 6-PHOSPHOGLUCONOLACTONASE

This application is a continuation of application Ser. No. 07/756,218, filed Sep. 4, 1991 now abandoned.

The invention concerns a stable 6-phosphogluconolactonase, EC 3.1.1.31, a process for the production of the enzyme as well as its use for the determination of clinically relevant parameters which can be converted into 6-phosphogluconolactone or which are directly or indirectly involved in its formation.

The invention particularly concerns a 6-phosphogluconolactonase (PGL) which has a good stability and which can be isolated from microorganisms such as Leuconostoc bacteria.

PGL—the systematic name is 6-phospho-D-glucono-1,5-lactone lactonohydrolase—catalyses the hydrolysis of 6-phosphogluconolactone to 6-phosphogluconate. 6-phosphogluconolactonase can therefore be used for the determination of 6-phosphogluconolactone and of reaction partners which can be converted directly or via several reaction steps into 6-phosphogluconolactone or for the determination of enzymes which catalyse the corresponding reactions. The PGL path is especially suitable for the determination of glucose, ATP and ATP-forming reaction partners. Thus two reduction equivalents are obtained from one mole of ATP by addition of 6-phosphogluconate dehydrogenase. Corresponding determinations can therefore be carried out with twice the sensitivity. This principle is described in the literature (Vormbrock and Helger, Enzyme 38, Suppl. 1, 20–21, 1987).

It is known that PGL occurs in yeasts as well as in various eukaryotic organs such as liver, kidney, erythrocytes, tissue and in several microorganisms.

PGL was first discovered in yeast extracts (Brodie and Lipman, J. Biol. Chem. 212, 677–685, 1955). Kawada et al. purified PGL from yeast whereby it was possible to achieve a purification of more than 130-fold (Biochem. Biophys. Acta 57, 404–407, 1962). However, this enzyme preparation did not have the necessary substrate specificity for quantitative determinations. A homogeneous enzyme preparation with improved properties in this regard could be isolated from bovine erythrocytes (Bauer et al., Eur. J. Biochem. 133, 163–168, 1983). The phosphogluconolactonase from microorganisms which has been investigated most is the enzyme from the bacterium Zymomonas mobilis (Scopes, FEBS Lett. 193, (2) 185–188, 1985). According to this PGL is present in Zymomonas mobilis in large quantities and can be isolated in a ca. 500-fold purification. In addition the Zymomonas enzyme has a good substrate specificity ($K_m$ 0.02–0.03 mmol/l).

However, a drawback of all the previously known PGL enzymes is that the stability of the isolated enzymes is insufficient and that the isolation of the enzymes from animal organs and from the described microorganisms is very complicated and time-consuming. Moreover, the required sources are mostly not available in sufficient quantity or only occur at a few special sites. In addition the described PGL enzymes from yeast do not have the required substrate specificity.

The object of the invention is therefore to provide a stable 6-phosphogluconolactonase which in addition is present in undemanding microorganisms that occur ubiquituously and are easy to culture.

This object is achieved by providing a 6-phosphogluconolactonase which still has at least 90% PGL residual activity after approximately 20 hours at pH 7.0 and 20° C. and which is obtainable from a Leuconostoc strain. As a rule the enzyme still has the full PGL initial activity after approximately 20 hours under the said conditions. Altogether the phosphogluconolactonase obtainable from Leuconostoc has a good activity between 20° and 30° C. and at a pH of 5.8 to 9.0. The optimal pH is at 6.5 to 7.0; the optimal temperature is constant between 20° and 30° C. The catalytic efficiency of PGL for 6-phosphogluconolactone with a Michaelis constant $K_m$ of less than 0.1 mmol/l complies with the required quality for quantitative determinations.

The invention also provides a process for the production of 6-phosphogluconolactonase from microorganisms by culturing them and isolating the enzyme from the biomass or from the culture broth which is characterized in that a Leuconostoc strain is cultured. Leuconostoc mesenteroides is preferably used and the publicly available Leuconostoc mesenteroides subspecies dextranicum (DSM 20187, NCIB 3355) is especially preferably used. "DSM" stands for Deutsche Sammlung yon Mikroorganismen und Zellkulturen GmbH, which is located at Moscheroder Weg 1b, D-3300 Braunschweig. "NCIB" stands for "National Collections of Industrial and Marine Bacteria Ltd.", P. O. Box 31, 135 Abbey Road, GB-Aberdeen, AB9 8DG (the name and address of this depository changed in 1988 and has since that time been abbreviated as "NCIMB"). DSM 20187 was deposited on Apr. 11, 1973.

The Leuconostoc strains according to the present invention can be cultured very simply on a medium containing glucose (or also lactose) as a carbon source and a yeast extract as a nitrogen source as well as salts and trace elements.

$MgSO_4$ and $K_2HPO_4$ among others can be used as suitable salts. Suitable trace elements are Mn and Fe among others.

Particularly high yields of PGL can be achieved if the substrate is fed continuously at 10°–37° C. and the pH is regulated at about 5.2–7.2.

The enzyme can be isolated according to the usual methods for enzyme purification as described for example in Eur. J. Biochem. 133, 163 ff (1983) and in FEBS Lett. 193, 185 ff. (1985). However, a purification procedure is preferred in which, after lysis by addition of lysozyme for example, a Polimin treatment and subsequently a fractionated ammonium sulfate precipitation is carried out and the $(NH_4)_2 SO_4$ fraction (ca. 1.4–3.2M) is chromatographed on phenyl sepharose. Subsequently a gel filtration is carried out for example on Sephacryl S200 or Superdex 200. Using this process, a PGL preparation is obtained in a yield of over 50% and with a specific activity of at least 500 U/mg protein. Individual enzyme preparations have a specific activity of approximately 1500 U/mg protein.

The enzyme purified in this way can be used directly for analytical purposes. PGL is of particular technical interest for the determinations of glucose-6-phosphate, glucose, ATP and ATP-forming enzyme reactions such as e.g. the enzymatic determination of creatine kinase or creatinine or creatine. All methods of determination in which 6-phosphogluconolactone is formed can be accelerated by PGL catalysis since 6-phosphogluconolactone is chemically rearranged only slowly to acid. The PGL which is added accordingly followed by 6-phosphogluconate dehydrogenase (6-PGDH) leads to an increase, in the ideal case to a doubling, of the sensitivity in a very much shorter time. Thus such coupled tests are of particular importance for parameters with a small measurement signal. This applies for example to CK-MB isoenzyme measurements in the serum or blood of cardiac infarct patients (Vormbrock and Helger, see above). Apart from the necessary auxiliary enzymes such as e.g. hexokinase (HK), glucose-6-phosphate dehydrogenase (G6PDH), PGL and 6-PGDH, NAD+ or NADP+ are additionally added as coenzyme. Which of the two coenzymes is used only depends on the source of the auxiliary enzymes G6PDH and 6-PGDH which are used but is of no importance for the PGL used from Leuconostoc. Thus 2 moles NADH or 2 moles NADPH, $CO_2$ and ribulose-5-phosphate are formed as final products of the enzyme cascade from 1 mole ATP. The NADH or NADPH formed is detected at a wavelength of 340 or 365 nm in a reflection photometer. The PGL according to the present invention from Leuconostoc is added in an amount of 0.2-0.5 U/ml test solution, preferably 0.3 U/test ml.

The addition of PGL in order to accelerate appropriate tests is particularly important when a G6PDH is used which does not contain any components which influence the PGL reaction which is for example the case with G6PDH produced by recombinant methods. As a result it is possible to add a defined amount of PGL, the acceleration of the reaction and thus the doubling of the measurement signal can be better calculated and as a consequence the corresponding tests are more reproducible.

A suitable diagnostic agent contains the PGL according to the present invention and the above-mentioned auxiliary enzymes or coenzymes. All constituents can be stored for approximately 24 hours at ca. 20° to 30° C. in a combined form and mixed directly with the sample to be examined shortly before carrying out the determination.

Figure 1:
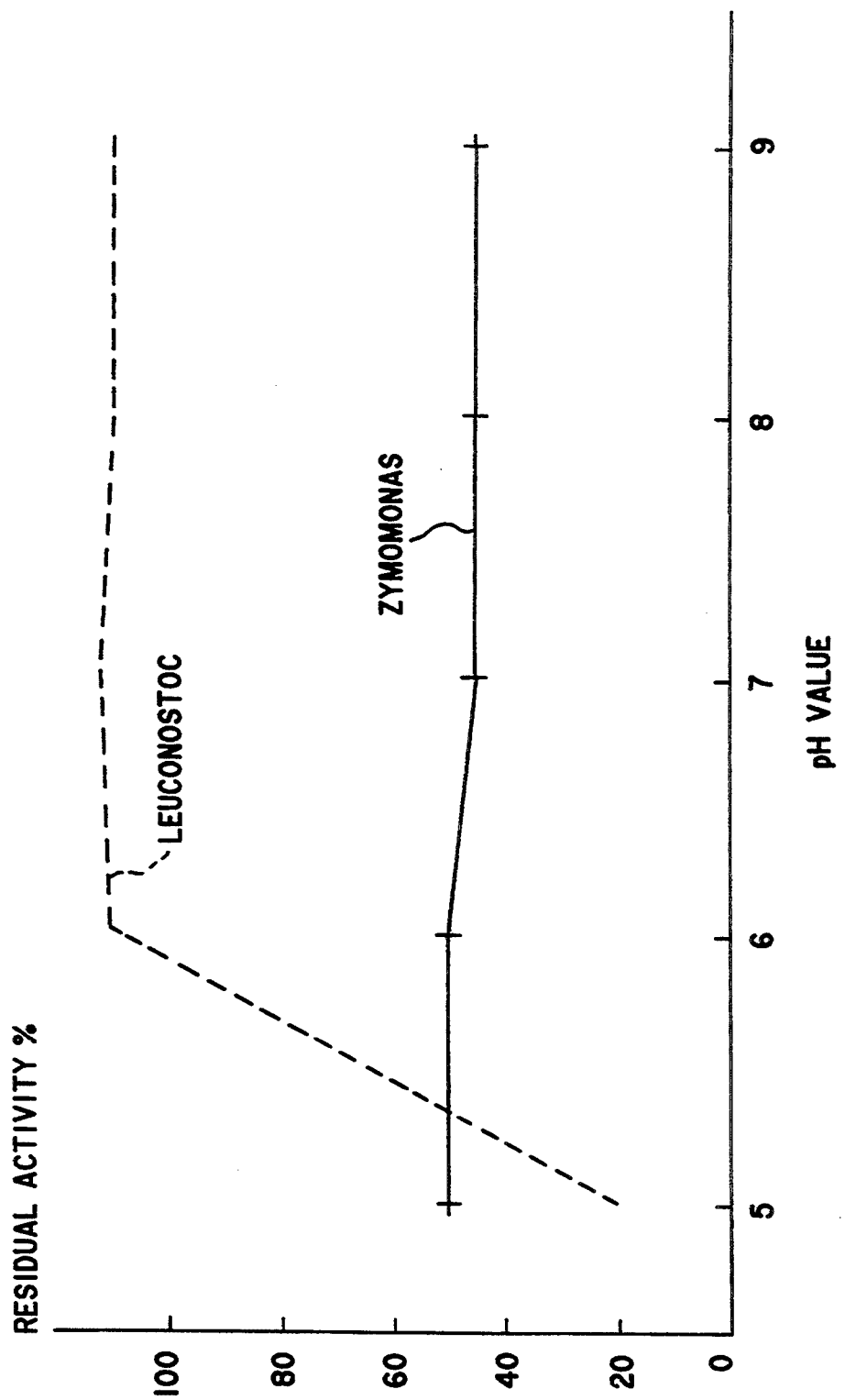
FIG. 1 pH stability: residual activity in % at an increasing pH at +20° C. for PGL from Leuconostoc and PGL from Zymomonas (0.2 U/ml PGL in 50 mmol/l potassium phosphate buffer; 2 hours)
Figure 2:
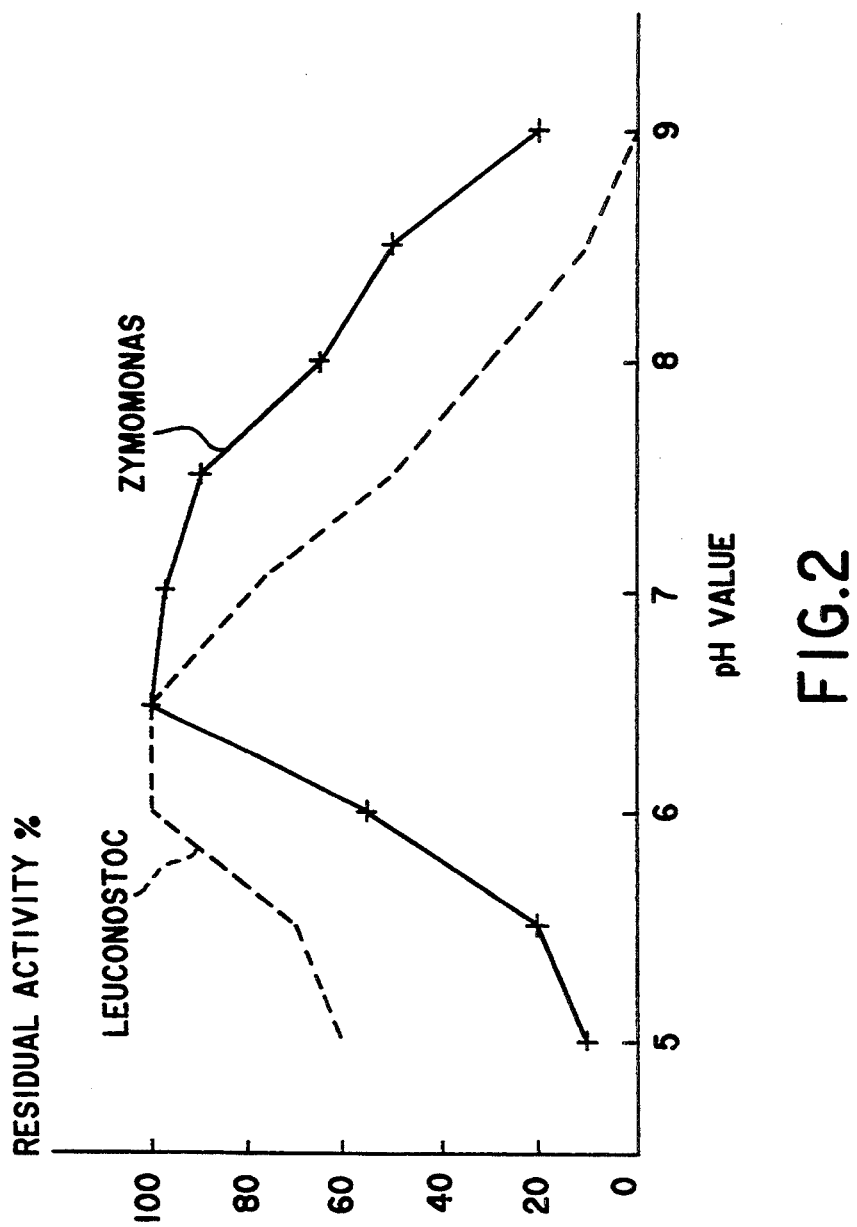
FIG. 2 Activity optimum: residual activity in % at an increasing pH at +25° C. for PGL from Leuconostoc and PGL from Zymomonas (0.1M MES, 2 mmol/l $MgCl_2$, 30 mmol/l NaCl) MES=4-morpholinoethanesulfonic acid FIG. 3 Temperature dependence: activity in U/mg with increasing temperature at pH 6.5 for PGL from Leuconostoc and PGL from Zymomonas.

The invention is elucidated further by the following examples:

EXAMPLE 1

Fermentation of Leuconostoc:

A culture medium containing yeast extract, glucose, salts and trace elements as the main components is steam-sterilized in a 100 l fermenter. The 100 l fermenter was innoculated with a 3 l culture of *Leuconostoc mesenteroides* sp. dextranicum DSM 20187 which had been previously cultured to an optical density of 3.

The 100 l culture was supplied with air at an aeration rate of 0.2 vvm and the temperature was kept constant at 25° C., the pH value of the culture was adjusted with sodium hydroxide solution to pH 6.8 during the whole process. In this process the PGL accumulates in the cells with increasing biomass. After 16 hours the bacteria were harvested in a Padberg centrifuge and the PGL was isolated from the cells.

EXAMPLE 2

Isolation of 6-phosphogluconolactonase (PGL) from Leuconostoc fermentation broth:

100 liters of *Leuconostoc dextranicum* fermentation culture was centrifuged. This resulted in 1470 g wet cell mass corresponding to 320 g dry mass. The biomass was suspended in 15 liters 10 mmol/l potassium phosphate buffer, pH 6.5, 7.35 g lysozyme was added and it was lysed for 12 hours at 20° C. For a complete lysis a high-pressure dispersion was carried out twice at 700 bar while cooling on ice. In order to separate the nucleic acids from the cell debris it was treated with 1.2% Polimin G 20 (polyethyleneimine) (BASF). The enzyme completely remains in the supernatant after centrifugation or filtration. Subsequently DEAE-Sephadex, equilibrated with 20 mmol/l potassium phosphate buffer, pH 6.5, was added to the enzyme solution and stirred for 60 min at +4° C. The anion exchanger was separated from the solution and eluted twice with 1 l 100 mmol/l potassium phosphate buffer containing 0.8 mol/l ammonium sulphate, pH 6.5 in each case. The combined eluates were fractionated with solid ammonium sulphate between 1.4 and 3.2 mol/l. The precipitated PGL precipitate was chromatographed on phenyl sepharose using a decreasing gradient (1.5 mol/l ammonium sulphate, 20 mmol/l potassium phosphate, pH 6.5). The enzyme is released from the column at ca. 1 mol/l ammonium sulphate. After concentrating the active fractions to 50 mg protein/ml at about +4° C. a PGL preparation with more than 500 U/mg protein was obtained after a subsequent molecular sieve passage through a Sephacryl S200 size exclusion gel filtration media column. PGL fractions with a specific activity of about 1500 U/mg can be obtained depending on the column material used.

Contamination with NADH oxidase, G6PDH, 6PGDH, ATPase, hexokinase, creatine kinase, phosphoglucomutase, glutathione reductase, phosphoglucose-isomerase, glucose dehydrogenase and glucose oxidase is in all cases less than 0.01% with respect to the PGL activity.

The enzyme is saturated with ammonium sulphate to 3.2 mol/l and stored at 10 mg protein/ml, pH 6.5, +4° C. and used in this form for analytical determinations.

TABLE 1

Purification of PGL from Leuconostoc (100 l culture)

| Step | KU | U/mg | Protein (g) | Yield [in %] |
|---|---|---|---|---|
| Lysozyme + high pressure | 1890 | 10 | 189 | 100 |
| G20 supernatant | 1500 | 44 | 34 | 79 |
| DEAE eluate | 1640 | 54 | 30 | 86 |
| AS fraction 1.4–3.2 M | 1600 | 64 | 25 | 84 |
| phenyl Sepharose eluate | 1250 | 290 | 4.3 | 66 |
| molecular sieve passage through Sephacryl S200 | 1050 | 590 | 1.8 | 55 |

EXAMPLE 3

Stability of PGL from Leuconostoc

A PGL fraction obtained according to Example 2 as well as the enzyme of Scopes isolated from Zymomonas are each kept at a concentration of 0.2 U/ml in 50 mmol/l potassium phosphate, pH 7.0 at 20° C. The enzyme activity remaining after 2 or 20 hours was determined (see Table 2.)

TABLE 2

| | Residual activity in % after 20 hours | |
|---|---|---|
| | Residual activity % | |
| | 2 h. | 20 h. |
| Zymomonas mob. | 45 | 0 |
| Leuconostoc dex. | 100 | 100 |

EXAMPLE 4

Determination of creatine kinase

I. Solutions
1. Buffer: imidazole (0.1 mol/l; pH 6.7), glucose (20 mmol/l), Mg acetate (10 mmol/l), EDTA (2 mmol/l)
2. Creatine phosphate solution (30 mmol/l)
3. ADP solution (2 mmol/l)
4. Hexokinase solution (2.5 U/ml)
5. NAD or NADP solution (2 mmol/l)
6. Glucose-6-phosphate dehydrogenase solution (1.5 U/ml)
7. PGL solution (1 U/ml)
8. 6-phosphogluconate dehydrogenase (1 U/ml)
Dilutions of the sample in imidazole buffer.

II. Procedure
Measurement at 365 nm; light path 1.0 cm; test volume 0.5 ml; temperature 37° C.; absorption coefficient $\epsilon = 3.4$ or 3.5 cm²/μmol. sample volume 0.02 ml;

III. Calculation $$\text{Vol. activity} = \frac{\Delta A/\min \times 0.5 \text{ ml} \times \text{dilution}}{\epsilon \times \text{vol. used [ml]}} = U/\text{ml sample}$$

IV. Result
The linearity, standard deviation in percent and thus the precision are comparable or better than the standard method e.g. "activated CK NAC" of Boehringer Mannheim (see Table 3).

TABLE 3

| Comparison of the CK-MB determination using a conventional method (1) with a method in which PGL is added (method 2) | | |
|---|---|---|
| | HS 1 | HS 2 |
| Method 1 x̄ | 24.7 | 15.8 |
| S | 1.8 | 2.1 |
| $C_V$ | 7.5 | 13.2 |
| n | 19 | 18 |
| Method 2 x̄ | 48.9 | 29.1 |
| S | 2.1 | 1.2 |
| $C_V$ | 4.2 | 4.3 |
| n | 19 | 18 |

HS 1, HS 2: 2 different, non-pathogenic human sera; x̄ = mean CK-MB activity in U/l ; S = standard deviation in U/l; $C_V$ = standard deviation in percent; n = number of measurements; method 1: "activated CK NAC", Boehringer Mannheim GmbH; method 2: ditto + 1U/ml 6-PGDH + 1 U/ml PGL.

Imprecision is often observed especially at low concentrations of CK-MB. The determination of CK-MB is improved by adding the corresponding enzyme and the consequent doubling of the NAD(P)H measurement signal. This is shown by the very much lower $C_V$ values of method 2 compared to method 1. The corresponding x values reflect the doubling of the measurement signal with an identical calculation factor. Therefore when calculating the CK-MB concentration the fact that two moles NADH or NADPH are formed per mole creatine phosphate must also be taken into consideration.

Other parameters such as e.g. ATP and glucose can be determined correspondingly.

We claim:
1. A purified 6-phosphogluconolactonase (PGL), wherein a PGL activity of at least 90% is present after about 20 hours at pH 7.0 and 20° C.
2. A purified 6-phosphogluconolactonase as claimed in claim 1, wherein the enzyme is purified from microorganisms of the genus Leuconostoc having PGL activity.
3. A purified 6-phosphogluconolactonase as claimed in claim 2, wherein the enzyme is purified from *Leuconostoc mesenteroides*.
4. A purified 6-phosphogluconolactonase as claimed in claim 3, wherein the enzyme is purified from the subspecies dextranicum (DSM 20187, NCIB 3355).
5. A purified 6-phosphogluconolactonase as claimed in claim 1, wherein the enzyme has the following characteristics:
   (1) optimal pH of 6.5–7.0;
   (2) optimal temperature of about 25° C.; and
   (3) Michaelis constant for 6-phosphogluconolactone of less than 0.1 mmol/l.
6. A process for producing 6-phosphogluconolactonase, comprising the steps of
   a) culturing microorganisms of the genus Leuconostoc,
   b) lysing the microorganisms,
   c) precipitating said 6-phosphogluconolactonase by fractionated precipitation, and
   d) purifying said 6-phosphogluconolactonase by chromatography.
7. The process according to claim 6, wherein the microorganisms are cultured at 10°–37° C. at a pH between 5.2–7.2.
8. The process according to claim 6, wherein said microorganisms are Leuconostoc mesenteroides dextranicum (DSM 20187, NCIB 3355).
9. A process for the determination of 6-phosphogluconolactone concentrations in a sample, comprising the steps of
   a) adding 6-phosphogluconolactonase to a sample suspected of containing 6-phosphogluconolactone, wherein said 6-phosphogluconolactonase retains 90% activity after 20 hours at pH 7.0 and 20° C.,
   b) adding hexokinase, glucose-6-phosphate dehydrogenase, 6-phosphogluconate dehydrogenase and a coenzyme selected from the group consisting of NAD+ (nicotinamide adenine dinucleotide) and NADP+ (nicotinamide adenine dinucleotide phosphate) to said sample, and
   c) detecting any reduced coenzyme formed by spectroscopic measurement, as an indication of the concentration of 6-phosphogluconolactone.
10. The process according to claim 9, wherein the amount of said 6-phosphogluconolactonase added is 0.2–0.5 U/ml solution.
11. The process according to claim 9, wherein the amount of said 6-phosphogluconolactonase added is 0.3 U/ml solution.
12. A process for the determination of compounds which are converted to form 6-phosphogluconolactone, comprising the steps of
   a) adding enzymes which catalyze the conversion of compounds into 6-phosphogluconolactone to a sample suspected of containing compounds from which 6-phosphogluconolactone can be formed,
b) adding 6-phosphogluconolactonase to said sample, wherein said 6-phosphogluconolactonase retains 90% activity after 20 hours at pH 7.0 and 20° C.,
c) adding hexokinase, glucose-6-phosphate dehydrogenase, 6-phosphogluconate dehydrogenase and a coenzyme selected from the group consisting of NAD+ (nicotinamide adenine dinucleotide) and NADP+ (nicotinamide adenine dinucleotide phosphate) to said sample, and
d) detecting any reduced coenzyme formed by spectroscopic measurement, as an indication of the concentration of compounds which are converted to form 6-phosphogluconolactone.

13. The process according to claim 12, wherein the compound to be determined is selected from the group consisting of creatinine, creatine, glucose and ATP (adenosine triphosphate).

14. A process for the determination of enzymes which convert compounds to form 6-phosphogluconolactone, comprising the steps of
a) adding compounds from which 6-phosphogluconolactone can be formed to a sample suspected of containing enzymes which convert compounds into 6-phosphogluconolactone,
b) adding 6-phosphogluconolactonase to said sample, wherein said 6-phosphogluconolactonase retains 90% activity after 20 hours at pH 7.0 and 20° C.,
c) adding hexokinase, glucose-6-phosphate dehydrogenase, 6-phosphogluconate dehydrogenase and a coenzyme selected from the group consisting of NAD+ (nicotinamide adenine dinucleotide) and NADP+ (nicotinamide adenine dinucleotide phosphate) to said sample, and
d) detecting any reduced coenzyme formed by spectroscopic measurement, as an indication of the concentration of enzymes which convert compounds into 6-phosphogluconolactone.

15. A composition for the detection of 6-phosphogluconolactone comprising
a) a purified 6-phosphogluconolactonase which retains 90% activity after 20 hours at pH 7.0 and 20° C.,
b) at least one enzyme selected from the group consisting of hexokinase, G6PDH (glucose-6-phosphate dehydrogenase) and 6-PGDH (6-phosphogluconate dehydrogenase), and
c) at least one coenzyme selected from the group consisting of NAD+ (nicotinamide adenine dinucleotide) and NADP+ (nicotinamide adenine dinucleotide phosphate).

16. A process for the determination of creatine kinase, comprising the steps of
a) adding compounds from which 6-phosphogluconolactone can be formed to a sample suspected of containing creatine kinase,
b) adding 6-phosphogluconolactonase to said sample, wherein said 6-phosphogluconolactonase retains 90% activity after 20 hours at pH 7.0 and 20° C.,
c) adding hexokinase, glucose-6-phosphate dehydrogenase, 6-phosphogluconate dehydrogenase and a coenzyme selected from the group consisting of NAD+ (nicotinamide adenine dinucleotide) and NADP+ (nicotinamide adenine dinucleotide phosphate) to said sample, and
d) detecting any reduced coenzyme formed by spectroscopic measurement, as an indication of the concentration of creatine kinase.

* * * * *